United States Patent [19]
Diao

[11] Patent Number: 5,640,975
[45] Date of Patent: Jun. 24, 1997

[54] SURGICAL DRAPE FOR USE IN UPPER EXTREMITY OPERATIONS

[76] Inventor: Edward Diao, 111 North Dr., Amherst, N.Y. 14226

[21] Appl. No.: 344,408

[22] Filed: Nov. 23, 1994

Related U.S. Application Data

[63] Continuation of Ser. No. 17,857, Feb. 16, 1993, abandoned.

[51] Int. Cl.$^6$ ............................................. A61B 19/08
[52] U.S. Cl. ...................................... 128/853; 128/849
[58] Field of Search .......................... 128/846, 849–856

[56] References Cited

U.S. PATENT DOCUMENTS

| | | | |
|---|---|---|---|
| 3,561,439 | 2/1971 | Bayer | 128/132 |
| 3,668,050 | 6/1972 | Donnelly | 128/893 X |
| 3,766,913 | 10/1973 | Balin | 128/132 D |
| 3,830,497 | 8/1974 | Krebs et al. | 128/853 |
| 3,856,005 | 12/1974 | Sislian | 128/853 X |
| 3,856,006 | 12/1974 | Krzewinski | 128/854 X |
| 4,059,104 | 11/1977 | DePriest et al. | 128/132 D |
| 4,119,093 | 10/1978 | Goodman | 128/132 D |
| 4,164,941 | 8/1979 | Knopick et al. | 128/132 D |
| 4,169,472 | 10/1979 | Morris | 128/854 |
| 4,379,192 | 4/1983 | Wahlquist et al. | 128/853 X |
| 4,524,767 | 6/1985 | Glassman | 128/132 D |
| 4,569,341 | 2/1986 | Morris | 128/853 |
| 4,586,498 | 5/1986 | Morris | 128/853 |
| 4,711,236 | 12/1987 | Glassman | 128/854 |
| 4,730,609 | 3/1988 | McConnell | 128/853 |
| 4,745,915 | 5/1988 | Enright et al. | 128/132 ED |
| 4,957,120 | 9/1990 | Grier-Idris | 128/849 |
| 4,974,604 | 12/1990 | Morris | 128/855 X |
| 5,002,069 | 3/1991 | Thompson et al. | 128/849 |
| 5,002,070 | 3/1991 | Taylor | 128/853 |
| 5,074,316 | 12/1991 | Dowdy | 128/853 X |
| 5,097,847 | 3/1992 | Mikhail et al. | 128/853 |
| 5,143,091 | 9/1992 | Patnode et al. | 128/853 |
| 5,161,544 | 11/1992 | Morris | 128/849 |
| 5,178,162 | 1/1993 | Bose | 128/849 |
| 5,222,507 | 6/1993 | Taylor | 128/853 X |
| 5,383,476 | 1/1995 | Peimer et al. | 128/853 X |

FOREIGN PATENT DOCUMENTS

| | | | |
|---|---|---|---|
| 2650501 | 2/1991 | France | 128/849 |

OTHER PUBLICATIONS

Drawings and statements submitted by Applicant on May 13, 1993, concerning Clinitek drape (Catalog No. 4947).

Primary Examiner—Robert A. Hafer
Assistant Examiner—Brian E. Hanlon
Attorney, Agent, or Firm—Edward W. Porter

[57] ABSTRACT

A surgical drape for use in surgery upon an upper extremity, in which a patient is placed upon an operating room, or OR, table and one of the patient's arms is laid out roughly perpendicular to his or her body on a hand table placed next to one side of the OR table. The drape comprises an OR table portion, formed of fabric, large enough to entirely cover the patient and to have peripheral edges which hang down around the OR table's circumference at least two feet below the table's top surface. The drape also includes a hand table portion, formed of fabric, large enough to cover the top of the hand table and to hang down around all the sides of that table which are not adjacent to the OR table at least one foot below the hand table's top surface. The drape includes means for joining the OR and hand table portions, so the hand table portion sticks out from a side of the OR table portion. Preferably, the hand table portion is fixedly attached to the OR table portion at least two feet from the edge of the OR table portion, and contains gussets which connect it to the OR table portion at locations nearer to that peripheral edge. This is done so the edges of both the OR and hand table portions are free to hang down toward the floor. The drape also includes an arm hole near where the OR and hand table portion are fixedly connected. This enables the patient's arm to pass through the arm hole and lie on top of hand table portion and the hand table beneath it. Preferably the hand table portion extends out from the middle of one of the long sides of the OR table portion, so that the drape can be used for surgery on either left or right upper extremities.

12 Claims, 5 Drawing Sheets

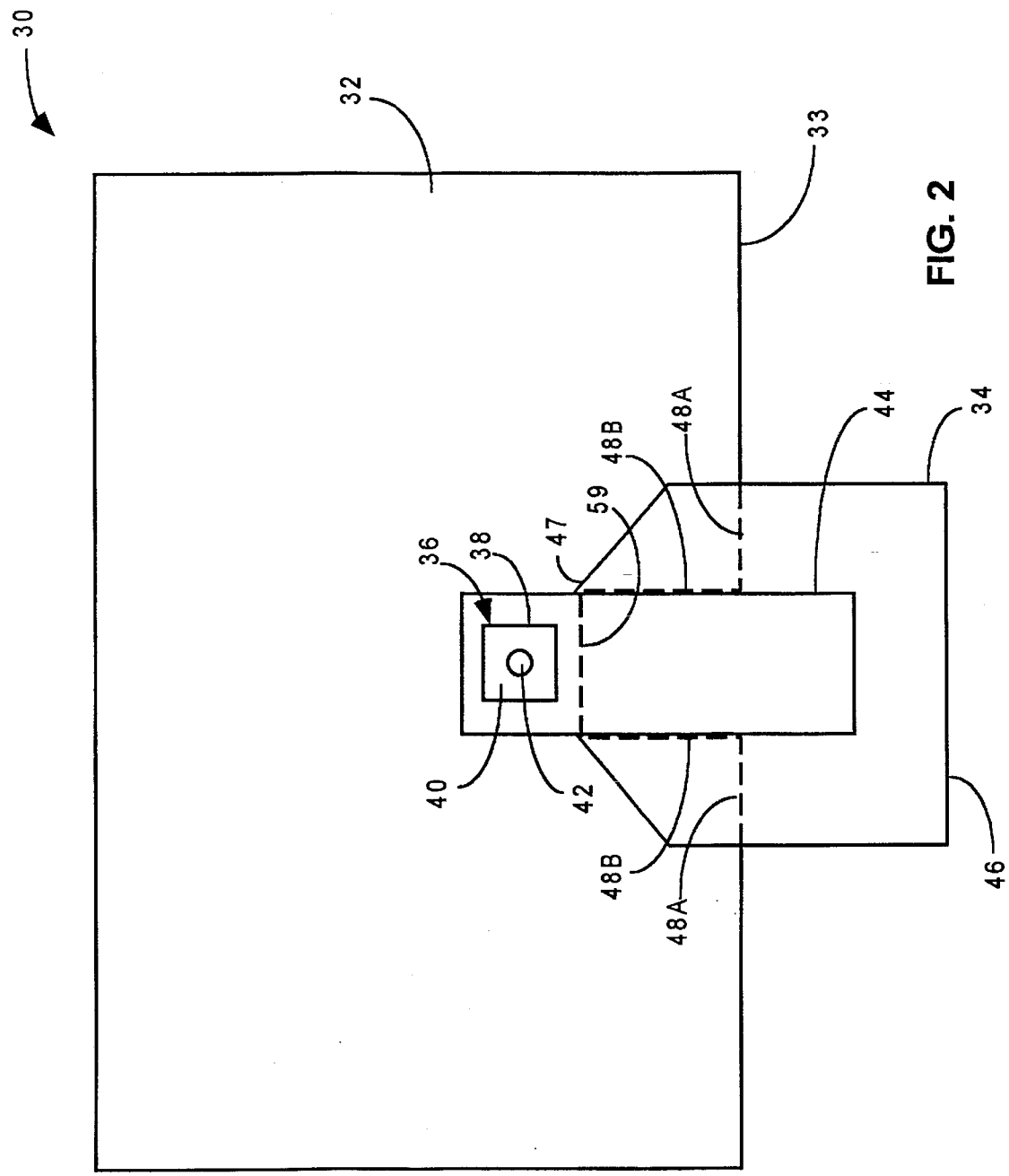

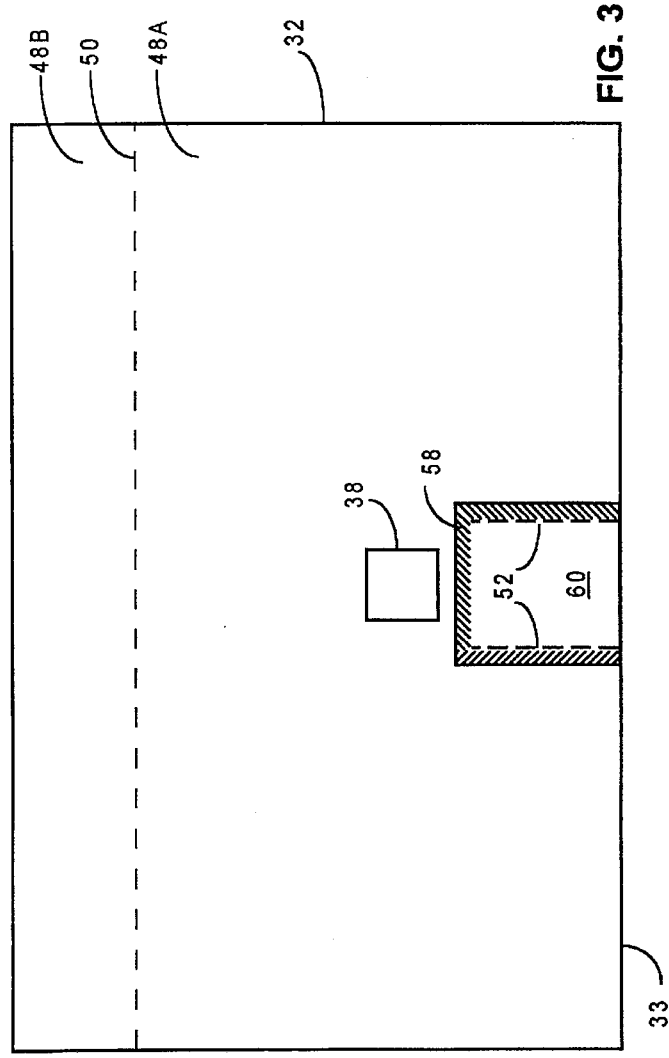
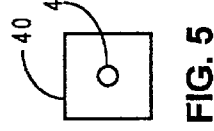
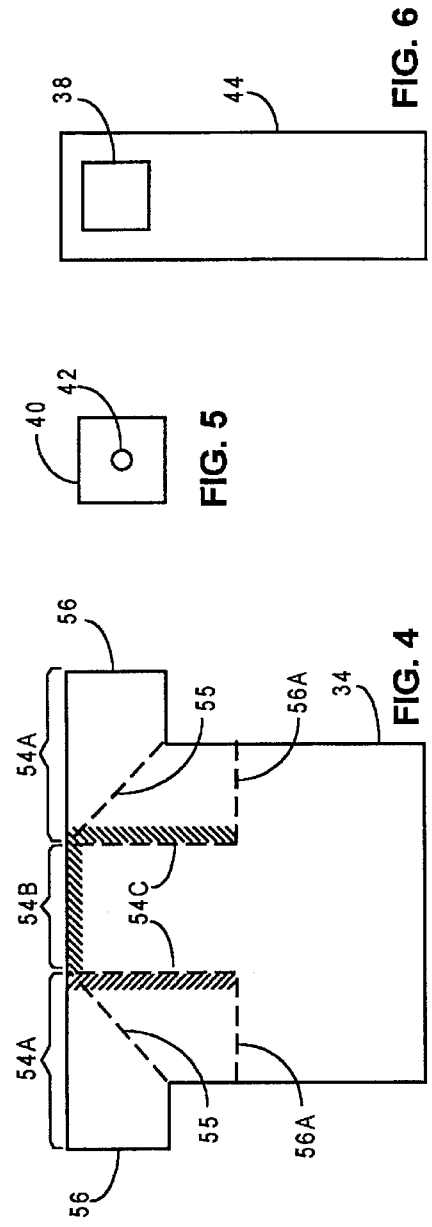

SURGICAL DRAPE FOR USE IN UPPER EXTREMITY OPERATIONS

RELATED APPLICATIONS

The present application is a file wrapper continuating application of U.S. patent application Ser. No. 08/017,857 filed by Edward Diao on Feb. 16, 1993, entitled "Surgical Drape For Use In Upper Extremity Operations" now abandoned.

FIELD OF THE INVENTION

The present invention relates to a surgical drape, and more particularly to such a drape designed for use in surgical operations upon patients' upper extremities, such as surgery upon hands, wrists, forearms, elbows, or upper arms.

BACKGROUND OF THE INVENTION

It is well known in the surgical arts to place surgical drapes over virtually all of the portions of a patient's body except for that upon which surgery is to be performed. Such drapes reduce that chance that bacteria and viruses from the rest of the patient's body will contaminate the portion being operated on, either directly, by contact with the medical personnel performing or assisting the operation, or movement in the air. Such drapes also have other purposes, such as keeping blood from covering the patients body, providing a visual barrier to the patient, so he or she does not see the operation, and providing special surfaces for absorbing blood and placing tools.

As is indicated in FIG. 1, when surgery is performed on a patient's upper extremity, such as surgery upon a hand, wrist, forearm, elbow, or upper arm, it is common to lie the patient 10 upon an operating room, or OR, table 12 and to place next to the OR table, adjacent the arm 14 to be operated on, a smaller table 16, called a hand table. The patient's arm is then stuck out roughly perpendicularly to its body so as to rest on this hand table. The surgeons then normally stand or sit next to the sides 18 or 20 of the hand table to perform the operation on the upper extremity.

Traditionally in the prior art, when such surgery has been performed, a flat, rectangular, one piece drape, with an arm hole in it, is placed over the patient's body, the OR table, and the hand table. The arm is placed through the arm hole, so that part of it can lie on top of the drape on the hand table. Unfortunately, such traditional prior art drapes were not large enough to cover both the entire top of the hand table and the entire top of the OR table. As a result, an extra drape would have to be clipped to the drape containing the arm hole, so as to cover the patient's lower legs and feet. As a result, the sterile barrier formed by such a drape was less than optimal. For example, if the clips holding the two drapes together came undone, a portion of the patient's body could become exposed. In addition, the use of one flat drape to cover both the OR table and the hand table resulted in an excess of fabric hanging at the sides of the hand table near where it meets the OR table.

SUMMARY OF THE INVENTION

It is an object of the invention to provide a one piece surgical drape for use in surgery upon an upper extremity which can cover the entire patient except the arm being operated on and the entire OR table and hand table.

It is another object of the invention to provide such a one piece surgical drape which will cover not only the tops of the OR and hand tables during surgery, but also will hang down around the sides of both those tables so as to form a better sterile barrier during an operation.

It is yet another object of the invention to provide a one piece surgical drape for use in surgery upon an upper extremity which allows both the OR table and hand table to be covered without excessive fabric at the side of the hand table near where it joins the OR table.

It is still another object of the invention to provide a one piece surgical drape for use in surgery upon an upper extremity which provides sturdy places on which to clip clamps for such purposes as holding tubing or wiring.

It is yet another object of the invention to provide a one piece surgical drape for use in surgery upon an upper extremity which provides a tough, absorbent surface over the top of the hand table for absorbing blood and other fluids released in the operation and which provides a safe surface for placing surgical implements.

It is still another object of the invention to provide a one piece surgical drape for use in surgery upon an upper extremity which enables the arm being operated upon to be moved without moving large portions of the rest of the drape.

It is yet another object of the invention to provide single one piece surgical drape which can be used for surgery upon either the fight or left upper extremity.

The present invention relates to one piece drape for use in surgery upon an upper extremity, such upon a patient's hand, wrist, forearm, elbow, or upper arm. The drape is intended for use in surgery in which a patient is placed upon an operating room, or OR, table, and one of the patient's arms is laid out roughly perpendicular to his or her body on a hand table placed next to one side of the OR table. The drape comprises an OR table portion, formed of fabric. This portion is large enough to entirely cover the patient and to have peripheral edges which hang down around the circumference of the OR table's top surface at least two feet. The drape also includes a hand table portion, also formed of fabric. This portion is large enough to cover the top of the hand table and to hang down around the sides of that table which are not adjacent to the OR table at least one foot below the hand table's top surface. The drape includes means for joining the two portions, so the hand table portion sticks out from one side of the OR table portion, enabling the drape to cover both tables at once. This means joins a central length of an edge of the hand table portion to the OR table portion at a location at least two feet from the peripheral edges of the OR table portion which hang down toward the floor when the drape is placed over the OR table. The drape also includes an arm hole near where the OR and hand table portions are connected. This enables the arm of a patient lying on the OR table and covered by the drape to pass through the arm hole and lie on top of hand table portion of the drape and the hand table beneath it.

Preferably the joining means includes gussets connecting the OR table portion and the attached edge of the hand table portion on both sides of that attached edge. These gussets enable the areas of the OR and hand table portions which hang down below the top of their respective tables to hang down in a relatively straight manner near where the two tables meet. It is also preferred that the arm hole be located in the OR table portion near its connection to the central length of the attached edge of the hand table portion. Preferably the arm hole include a window hole in the fabric of the drape which is larger than the diameter of most human arms, an elastic membrane lying across the window hole; and a hole in that elastic membrane smaller than the diameter of most human arms. As a result, when the patient's arm is stuck through the arm hole, the elastic material will press against the sides of that arm so as to form a sterile barrier during the operation.

It is also preferred that the length of the hand table portion in the direction which sticks out from the side of the OR table portion be sufficiently long, that if the arm is stuck through the arm hole near the arm's elbow, the drape can be folded back under the arm at least three inches toward the patient's arm pit and still extend out across the top of the hand table and hang down at least one foot below the edge of its far end. It is further preferred that the surgical drape include a pad of material which is more absorbent and tougher than the fabric of which the OR and hand table portion are made. This pad is attached to the hand table portion in a location so that the arm which sticks out through the arm hole will lie upon it. The pad is preferably of sufficient size to cover the top of the entire hand table, even when the drape is folded back under the patient's arm toward the arm pit by at least three inches. Preferably the pad extends around the arm hole, so clamps for holding tubing or wiring can be clipped to its relatively tough material adjacent said arm hole. In the preferred embodiment, the pad is joined to the fabric of the drape in such a manner that at least one-quarter inch of the outer edge of that pad can be bent up away from the fabric, making it easier to clip clamps to the edge of the pad. It is also preferred that the fabric used for both the OR and hand table portions be sufficiently tough that clamps which do not bear much weight can clipped to it without tearing.

DESCRIPTION OF THE DRAWINGS

These and other aspects of the present invention will become more evident upon reading the following description of the preferred embodiment in conjunction with the accompanying drawings, in which:

FIG. 2 is a top view of a preferred embodiment of the surgical drape of the present invention as it would appear if laid upon a large flat surface;

FIG. 3 is a top view of the piece of fabric used in the OR table portion of the preferred embodiment shown in FIG. 2:

FIG. 4 is a top view of the piece of fabric used in the hand table portion of the preferred embodiment shown in FIG. 2:

FIG. 5 is a top view of the elastic membrane used in the arm hole of the preferred embodiment shown in FIG. 2;

FIG. 6 is a top view of the tough, absorbent pad used in the preferred embodiment shown in FIG. 2;

DETAILED DESCRIPTION OF THE PREFERRED EMBODIMENT

Figure 1:
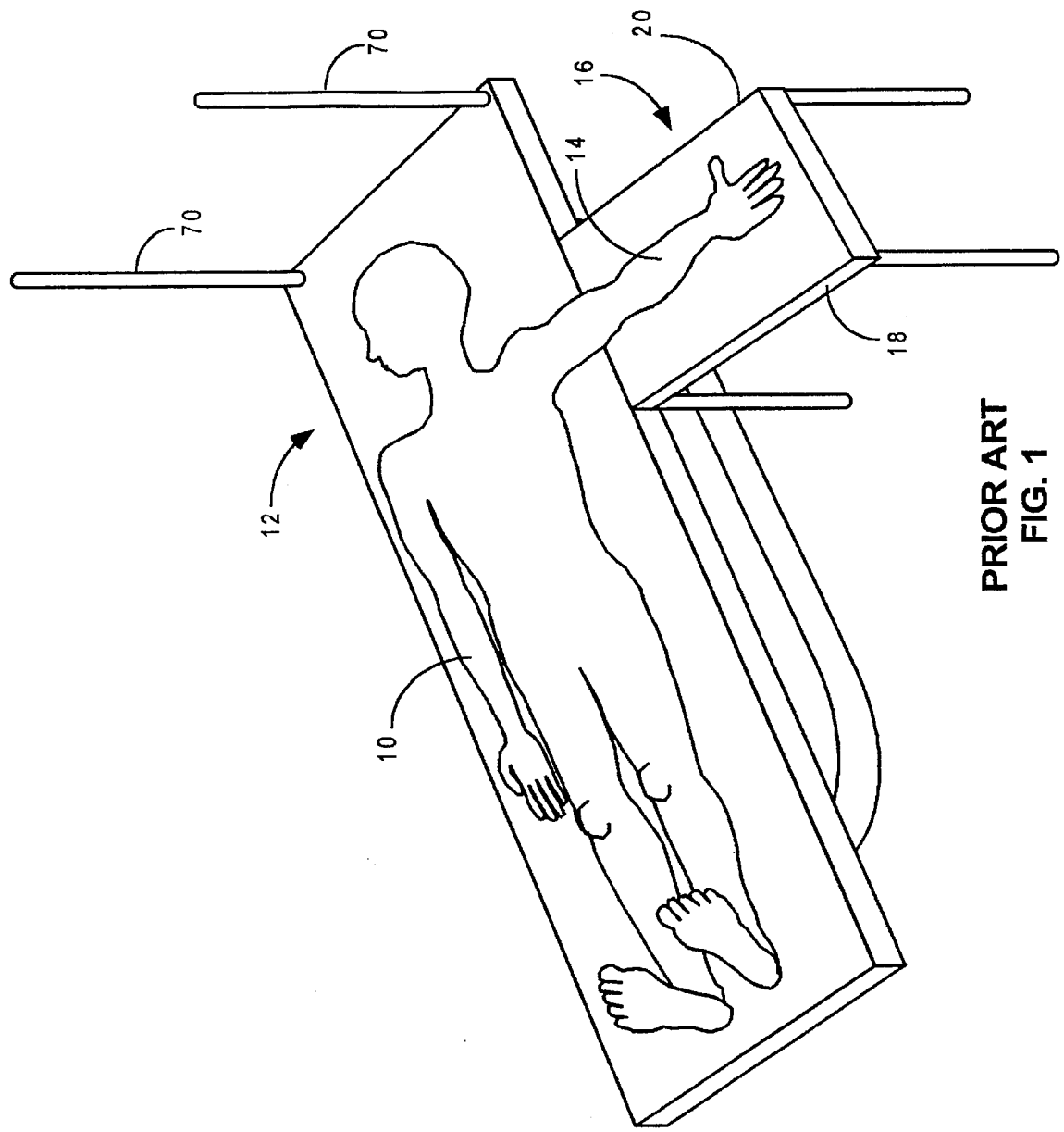
FIG. 1 is a perspective view of a patient lying upon an OR table with an arm stuck out perpendicularly onto a hand table, which is a traditional position during surgery upon an upper extremity and which is the position for which the surgical drape of the present invention has been designed.

FIG. 2 shows how a preferred embodiment of the surgical drape of the present invention looks when laid out upon a large flat surface. The drape 30 includes a large rectangular OR table portion 32, approximately one-hundred and sixty-eight inches long by one hundred inches wide. This portion is designed to cover an OR table having a patient lying upon it with enough fabric so that the peripheral edges of its rectangle could hang down around substantially the entire circumference of the top edge of the OR tablet by at least two feet. In preferred embodiment of the invention the OR table portions should be formed of a rectangularly shaped piece of fabric at least one hundred and sixty inches long and at least ninety inches wide. Having a drape this large improves the quality of the sterile barrier created by the drape, since is decreases the chance that any covered portion of the patient's body will become exposed, that any of the medical personnel performing the surgery will touch undesired portions of the patient or the OR table, or that bacteria or viruses will be transmitted by air from the covered portion of the patient during the operation.

FIG. 2 also shows a generally rectangular extension 34 to the drape 30. This extension is called the hand table portion, since it is designed to cover the hand table or armboard which is placed at the side of the OR table during surgery upon an upper extremity. The hand table portion 34 is approximately sixty inches wide (in the direction parallel to the long axis of the OR table portion 32) by sixty-six inches long (from hand table portion's bottom edge 46 to its top-most point 47 shown in FIG. 2). When the drape is laid flat, as shown in FIG. 2, approximately thirty-three inches of the sixty-six inch length of the hand table portion extends out perpendicularly past the middle of one of the OR table portion's long sides, the long side 33 shown in FIG. 2. The hand table portion is large enough to cover the entire top of a standard hand table and to hang down at least one foot over all the edges of that table, except that next to the OR table. This assures that the top most portions of the hand table will not be exposed during the operation, even if the drape shifts slightly.

The drape also includes an arm hole 36. This arm hole comprises a window-shaped cut 38 in the fabric of the OR table portion. An elastomeric film, or membrane, 40 is laid across this window 38. The elastic membrane has a hole 42 in its center. The window 38 is approximately ten inches square, substantially larger than the diameter of most human arms. The hole 42 is approximately two inches in diameter, substantially smaller than the diameter of most human arms.

The center of the arm hole in the elastic membrane is at least six inches closer to the long axis of the OR table portion than the nearest portions of the gussets which connect the OR and hand table portions. Thus, it can be seen that most human arms can stick through the arm hole 36, but will have the elastic film 40 stretch tight around them, so that a sterile barrier will be formed with such arms.

In the preferred embodiment the fabric of both the OR and hand table portions of the drape is EVOLUTION®, a non-absorbent, non-woven polypropylene fabric made by Kimberly-Clark Corporation, 1400 Holcomb Bridge Road, Roswell, Ga. 30076. Although other drape fabrics could be used with the present invention, EVOLUTION® is preferred because it provides a good barrier, not only to most liquids, but also to bacteria. Preferably a sufficiently heavy grade of this fabric is used to enable clamps which do not exert much force to be clipped to the fabric without tearing. In the preferred embodiment, the elastic membrane of the arm hole 36 is made of KRATON, an elastomeric chemical which had been trademarked by Shell Oil Company. Elastomeric films made of KRATON of the type used in the preferred embodiment can be obtained from Clopay Corporation, 312 Walnut Street, Cincinnati, Ohio 45202. Elastic films made of material other than KRATON could be used with the present invention, provided they form a sterile barrier, have sufficient strength not to rip when an arm is placed through them, and have enough elasticity to form a tight sterile barrier around the arm.

Figure 8:
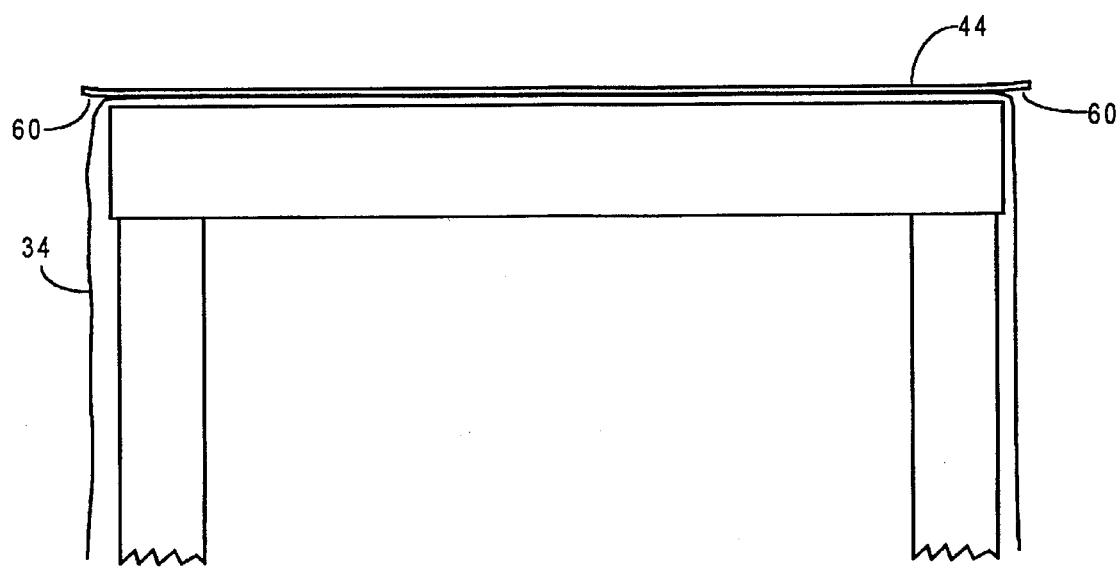
FIG. 8 is a cross sectional view of the hand table part of the surgical drape shown in FIG. 7 viewed along cross section 8—8 of FIG. 7.

The drape 30 also includes a pad 44 formed of a tough, absorbent material. This pad is twenty-four inches wide. It extends around the arm hole 36 and extends out from the window 38 of that hole approximately 50 inches down the center of the hand table portion 34, toward the furthest edge 46 of that portion. This makes the pad large enough to cover the entire width and length of most hand tables. In the preferred embodiment, this pad is made of a layer of CONTROL® PLUS, which is also made by Kimberly-Clark Corporation. This material contains an upper layer of non-woven absorbent fabric bonded to a lower layer formed of a liquid impervious film. Its absorbent fabric is designed to absorb blood or other fluids which might be released during an operation upon an upper extremity. Its impervious layer not only provides an additional barrier to the liquids absorbed by its absorbent material so as to prevent potential contamination of the hand table below the pad, but increases the toughness of the pad. This reduces the chance that the pad will be accidentally cut by surgical instruments, makes the pad a safe place to place such instruments, and makes the pad tough enough to clip clamps to, even if those clams are expected to exert a relatively large force upon the drape. Preferably, one-quarter to one-half inch of the pad near its edge 60 is not attached to the fabric of the drape, as is shown in FIG. 8 so that clamps can be easy clipped around the edge of that pad. The pad 44 is placed around the arm hole 36, in part, because it is common to place clamps holding wiring or tubing near the arm hole when performing surgery upon an upper extremity.

The dotted lines 48A and 48B shown in FIG. 2 are used to indicate the two gussets, or folds, which connect the parts of the OR table portion which hang down below the top of the OR table to adjacent parts of the hand table portion which hang down below the top of the hand table. The shape of these gussets can be better understood with regard to FIGS. 3 and 4.

FIG. 3 shows the shape of the fabric of which the OR table portion 32 is formed. It shows the cut for the arm hole window 38. It also shows a dotted line 50, indicating where a strip of fabric 49B is attached to a much wider strip 49A, so as to add an extra twelve inches to the width of the OR table portion. Finally, it shows two dotted lines 52. These indicates cuts made to form the two gussets which connect to the hand table portion 34.

FIG. 4 shows the shape of the fabric of which the hand table portion 34 is made. As shown in FIG. 4, this fabric has a "T" shape. The top edge of this fabric, labeled 54A and 54B is called the attached edge of the hand table portion, since it is attached to the OR table portion. The top left and right extensions of the "T" shape shown in FIG. 4 are each folded at a forty-five degree angle about lines 55. This causes the left and right lengths 54A of the attached edge to fold down under the main surface of the hand table portion 34, as is indicated by the dotted lines 54C. Similarly the side edges 56 of the left and right "T" extensions fold down under the main surface of the hand table portion to the positions indicated by the dotted lines 56A. Then the top of hand table portion 34, as shown in FIG. 4, is moved up approximately thirty inches above the bottom edge 33 of the OR table portion 32, as shown in FIG. 3, so the two portions 32 and 34 have the relative positions shown in FIG. 2. Then the folded lengths 54C of the hand table portion's attached edge, shown in cross hatching in FIG. 4, are glued to the edges of the cuts 52 shown in cross hatching in FIG. 3. At the same time the central length 54B of the hand table portion's attached edge, show in cross hatching in FIG. 4, is similarly glued to the cross hatched portion 58 of the OR table portion shown in FIG. 3.

Since the cuts 52 shown in FIG. 3 are each thirty inches long, the central length 54B of the hand table's attached edge is more than two feet from the nearest peripheral edge 33 of the rectangle formed by the OR table portion. As a result of the gusseted connection formed by the gluing between the OR and hand table portions, the central part of the hand table portion 34, that covered by the pad 44, shown in FIG. 1, is able to stick out perpendicularly from the side of the OR table portion which hangs down vertically over the edge of the OR table along the line indicated by the dots 59 in FIG. 2.

In the preferred embodiment, the flap of fabric 60 formed between the two cuts 52, shown in FIG. 3, is glued to the underside of the hand table portion (although this is not indicated in FIG. 4). In other embodiments of the invention, this flap of fabric could be cut out. In this case, I would not consider any edge formed by such a cut out to be a "peripheral edge" of the OR table portion as that phrase is used in the claims that follow, since it would not be one of the outer most edges of the OR table portion.

FIG. 5 shows the shape of the elastic membrane 40 used in the arm hole 36, and FIG. 6 shows the shape of the tough absorbent pad 44. As is indicated in FIGS. 3, 5, and 6, the elastic membrane 40 is slightly larger than the arm hole window 38 in the fabric of the OR table portion 32 or pad 44. This is so the fabric of both the OR portion and the pad around the edge of the arm hole window 38 can be glued to the outer edges of the elastic membrane, so as to hold it in place. The pad 44 is glued to the upper surface of the OR and hand table portions, 32 and 34, respectively, in the position indicated in FIG. 2. As stated above, it is preferred that such glue not be applied all the way to the edges of the pad 44, so as to leave one-quarter to one-half inch of the outer edge of that pad material free from attachment to the main fabric of the drape, so clamps can be more easily clipped to those outer edges.

Figure 7:
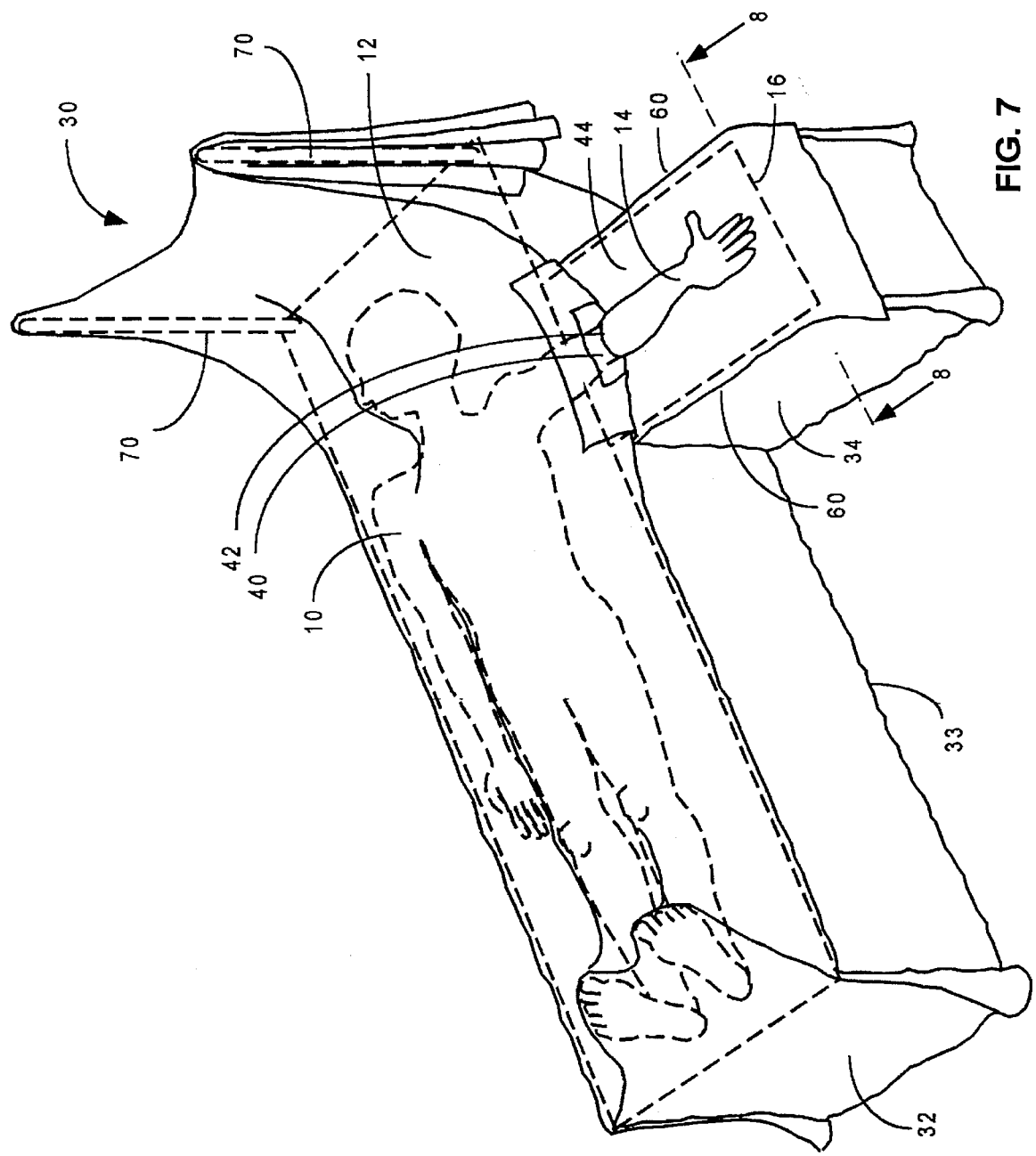
FIG. 7 is a perspective view of the surgical drape of the preferred embodiment when placed over the patient, OR table, and hand table shown in FIG. 1

FIG. 7 illustrates how the drape 30 looks when actually placed over an OR table 12 and a hand table 16 upon which a patient 10 has been placed. The top of the OR and hand tables, and the portion of the patient covered by the drape are all shown in dotted lines. The OR table portion 32 is sufficiently large that it not only covers the patient 10 and the top of the operating table 12, but also has enough fabric to hang down at least two feet around the entire top edge of the table 12. In FIG. 7, is should be noted that two poles 70 have been placed at the top two corners of the OR table. This has been done to hold the end of the drape over the patient's head up, so an anesthesiologist can administer to the patient without moving the drape. It can be seen from FIG. 7, and from the very large dimensions given for the OR table portion 32, that this portion of the drape would have enough fabric to hang down over two feet over the top of the OR table, were the poles 70 not in use. In fact, the use of the poles 70 requires this excess fabric, since they stick up from the OR table by approximately two feet themselves.

In FIG. 7, the hand table portion 34 of the drape hangs down on three sides of the hand table 16 by more than one foot. The arm 14 of the patient sticks out through the hole 42 in the elastic membrane 40 of the arm hole. The elastic material of the membrane 40 has stretched tightly around the arm to make a sterile barrier at the arm hole. The pad 44 is large enough to cover the entire top surface of the hand table, and lies underneath the arm. As is indicated in FIG. 7, it is preferred that a portion of the drape be folded back toward the patient's arm pit, under the arm, below the arm hole by three to nine inches. This is done to create a gathering of loose fabric around the arm hole which can move when the arm is moved without requiring the movement of other parts of the OR or hand table portions. In the preferred embodiment, the size of the OR table portion 32, the hand table portion 34, and the pad 44 have all been made larger so that this gathering of loose fabric can be provided while still enabling the OR table to be fully covered and surrounded by an overhang of two or more feet, and the hand table to be fully covered by the pad 44, and fully covered and surrounded by an overhang of one or more feet by the hand table portion 34.

FIG. 7 also provides and illustration of how the connection between the OR and hand table portions described above allows the center of the hand table portion, that part of it covered by the pad 44, to stick out at a ninety degree angle relative to the sides of the OR table portion which hang down over the sides of the OR table, while at the same time allowing the sides of the hand table portion which hang down over the edge of the hand table to also hang down in relatively straight manner. In addition, the gusseted connection between the OR and hand table portions cause the parts of the OR table portion and the hand table portion which hang down adjacent to each other to be firmly glued to each other, creating a good sterile barrier around both the OR and hand tables.

As is shown in FIG. 2, the hand table extension 34 is placed in the middle of one of the long sides of the OR table portion 32. This is done, even though the human arm is not in the middle of the body, so that one drape 30 can be used for operations upon either the left or right upper extremity. In the preferred embodiment, the long dimension of OR table portion extends seventy-two inches on either side of the twenty-four inch width of the pad 44. This seventy-two inch length is more than long enough for either end of OR table portion to reach all the way from the hand table down to the end of the operating table at which a patient's feet are located. Thus, either end of the OR table portion can be used to cover a patient's body from his shoulder to his feet, and either end can be used to cover the much shorter distance from his or her shoulders to his or her feet. It is preferred that in other embodiments of the invention both the arm hole and the connection between the OR table portion and the hand table portion are located so the length of the OR table portion extends at least 80 inches on either side of the arm hole, enabling either end of the OR table portion to extend from the hand table down to cover and drape over the feet of virtually all patients, and thus enabling the drape to be used for surgery upon either a left or right upper extremity. Having one drape that can be used for surgery upon either left or right upper extremities is a major benefit, since it significantly cuts the number of upper extremity drapes which have to be stocked by hospitals, clinics, or doctors which perform surgery upon upper extremities.

It should be understood that the forgoing descriptions and drawings are given merely to explain and illustrate the invention and that the invention is not to be limited thereto, except in so far as the interpretation of the appended claims are so limited. Those skilled in the art who have the disclosure before them will be able to make modifications and variations therein without departing from the scope of the invention.

For example, those skilled in the surgical arts will understand that many OR tables have armboards which can be pulled out from either side of such OR table to function as hand tables, and for purposes of this invention such armboards should be considered a type of hand table.

It should also be understood that different fabrics and materials can be used than the trademarked EVOLUTION®, CONTROL® PLUS, and KRATON™ materials used in the preferred embodiment described above. It should also be understood that different types of arm holes than that described above could be used with the present invention. Furthermore, it should be understood that the precise size and shape of the various parts of the surgical drape of the present invention can be changed without departing from the invention's intended scope, and that various subcombinations of the features disclosed in the preferred embodiment are also covered by that intended scope.

What I claim is:

1. A surgical drape for use in surgery upon an upper extremity in which a patient is laid along the top surface of an elongated operating table having two long opposite sides extending along the operating table's length and one of the patient's arms is laid out roughly perpendicular to his or her body on the top surface of a hand table placed next to one of the long sides of said operating table, said drape comprising:

an operating table part, made of fabric, which is sized and shaped so said operating table part can entirely cover said patient and the top surface of the operating table and have said part's outer edges hang down below the top surface of the operating table on both of the operating table's long sides;

a hand table part, made of fabric, large enough to cover the top of said hand table and to hang down on the sides of the hand table which are not adjacent the operating table;

a connection between said operating and hand table parts, said connection including:

a hinging connection which connects the hand table part to the operating table part along a line which extends parallel to the length of the operating table when the operating table part is positioned upon said operating table and the hand table part is placed upon the hand table adjacent said long side of the operating table, said hinging connection having two ends and being positioned at least two feet away from the nearest portion of the operating table part's outer edge;

two cut edges on said operating table part, each of which extends in a generally perpendicular direction relative to said hinging connection from a respective one of said hinging connection's two ends toward the outer edge of the operating table nearest said hinging connection, said cut edges enabling the operating table part to hang down straight over the sides of the operating table on both sides of the hand table without requiring that said operating table part similarly hang down between the operating and hand tables; and gusset connections which connect the hand table part to the operating table part on both sides of said hinging connection along each of said two cut edges, so as to form gussets which enable the portions of the operating and hand table parts which hang down below the top surfaces of their respective tables when said drape is placed upon said tables to hang down in a relatively perpendicular manner from the two ends of the hinging connection; and an arm hole in the operating table part, said arm hole being located adjacent said hinging connection in a position that is further from the nearest portion of the operating table part's outer edge than said hinging connection is from said operating table part's outer edge so that, when said drape is used to cover a patient lying on said operating table and to cover said hand table, the patient's arm can pass through said hole and can lie on top of the hand table part which is placed on said hand table.

2. A surgical drape as in claim 1, wherein the center of said arm hole is at least six inches closer to the center of said operating table part than is the hinging connection.

3. A surgical drape as in claim 1, further including a pad made of material which is more absorbent and more resistant to cutting and tearing than the fabric of which said operating and hand table parts are made, said pad being attached to said hand table part in an elongated area extending substantially perpendicularly from the hinging connection so that when said arm extends out through said arm hole from under said drape said arm will lie upon said pad.

4. A surgical drape as in claim 3:
   wherein said pad extends in a line from around the arm hole on the operating table part, past the hinging connection, and onto the portion of the hand table part which is intended to lie on top of said hand table; and
   wherein said pad is connected to said fabric of said operating and hand table parts in such a manner that at least one-quarter inch of an outer edge of said pad is not fixedly attached and can be bent up away from said fabric, making the clipping of clamps to said outer edge easier.

5. A surgical drape as in claim 1, wherein said arm hole includes:
   a window hole in said operating table part larger than the diameter of said patient's arm;
   an elastic membrane lying across said window hole;
   a hole in said elastic membrane smaller than the diameter of said patient's arm, so that when said patient's arm is extended through said hole in said elastic membrane, said elastic material will press against the sides of said arm so as to form a sterile barrier during the operation.

6. A surgical drape as in claim 1 wherein said operating table part has a length which is intended to lie along the length of said operating table of at least one-hundred-and-sixty inches and a width of at least ninety inches.

7. A surgical drape for use in surgery upon an upper extremity in which a patient is laid along the top surface of an elongated operating table having two long opposite sides extending along the operating table's length and one of the patient's arms is laid out roughly perpendicular to his or her body on the top surface of a hand table placed next to one of the long sides of said operating table, said drape comprising:
   an operating table part, made of fabric, which is sized and shaped so said operating table part can entirely cover said patient and the top surface of the operating table and have said part's outer edges hang down below the top surface of the operating table on both of the operating table's long sides;
   a hand table part, made of fabric, large enough to cover the top of said hand table and to hang down on the sides of the hand table which are not adjacent the operating table;
   a connection between said operating and hand table parts, said connection including:
      a hinging connection, which connects the hand table part to the operating table part along a line which extends parallel to the length of the operating table when the operating table part is positioned upon said operating table and the hand table part is placed upon the hand table adjacent said long side of the operating table, said hinging connection having two ends and being positioned at least two feet away from the nearest portion of the operating table part's outer edge;
      two cut edges on said operating table part, each of which extends in a generally perpendicular direction relative to said hinging connection from a respective one of said hinging connection's two ends toward the outer edge of the operating table nearest said hinging connection, said cut edges enabling the operating table part to hang down straight over the sides of the operating table on both sides of the hand table without requiring that said operating table part similarly hang down between the operating and hand tables; and
      gusset connections which connect the hand table part to the operating table part on both sides of said hinging connection along each of said two cut edges, so as to form gussets which enable the portions of the operating and hand table parts which hang down below the top surfaces of their respective tables when said drape is placed upon said tables to hang down in a relatively perpendicular manner from the two ends of the hinging connection; and
   an arm hole in said drape having a center at least six inches further from the nearest portion of the operating table part's outer edge than said hinging connection is from said operating table part's outer edge, and being located adjacent said hinging connection so that, when said drape is used to cover a patient lying on said operating table and to cover said hand table, the patient's arm can pass through said hole and can lie on top of the hand table part which is placed on said hand table;
   a pad made of material which is more absorbent and more resistant to cutting and tearing than the fabric of which said operating and hand table parts are made, said pad being attached to said hand table part along an area extending out perpendicularly from the hinging connection.

8. A surgical drape as in claim 7, wherein:
   said pad extends from the hand table part to around the arm hole on said operating table part; and
   said pad is connected to said fabric of said drape in such a manner that at least one-quarter inch of an outer edge of said pad is not fixedly attached to said fabric and can be bent up away from said fabric, making the clipping of clamps to said outer edge easier.

9. A surgical drape for use in surgery upon an upper extremity in which a patient is laid along the top surface of an elongated operating table having two long opposite sides extending along the operating table's length and one of the patient's arms is laid out roughly perpendicular to his or her body on the top surface of a hand table placed next to one of the long sides of said operating table, said drape comprising:
   an operating table part, formed of fabric having a generally rectangular shape having a length of at least one-hundred-and-sixty inches and a width of at least ninety inches, and having a central axis which extends along the length of said rectangular shape in the middle of said width;

a hand table part, formed of a fabric large enough to cover the top of said hand table and to hang down on the sides of the hand table which are not adjacent the operating table;

a connection between said operating and hand table parts, said connection including:

a hinging connection which connects the hand table part to the operating table part along a line which extends parallel to the length of the operating table part, said hinging connection having two ends and being positioned at least two feet away from the nearest portion of the operating table part's outer edge;

two cut edges on said operating table part, each of which extends in a generally perpendicular direction relative to said hinging connection from a respective one of said hinging connection's two ends toward the outer edge of the operating table nearest said hinging connection, said cut edges enabling the operating table part to hang down straight over the sides of the operating table on both sides of the hand table without requiring that said operating table part similarly hang down between the operating and hand tables; and gusset connections which connect the hand table part to the operating table part on both sides of said hinging connection along each of said two cut edges, so as to form gussets which enable the portions of the operating and hand table parts which hang down below the top surfaces of their respective tables when said drape is placed upon said tables to hang down in a relatively perpendicular manner from the two ends of the hinging connection; and an arm hole in said drape having a center at least six inches closer to the central axis of the operating table part than the hinging connection is from said central axis, and being located adjacent said hinging connection so that, when said drape is used to cover a patient lying on said operating table and to cover said hand table, the patient's arm can pass through said hole and can lie on top of the hand table part which is placed on said hand table;

a pad made of material which is more absorbent and more resistant to cutting and tearing than the fabric of which said operating and hand table parts are made, said pad being attached to said hand table part along an area extending out perpendicularly from the hinging connection.

10. A surgical drape as in claim 9, wherein:

said pad extends from the hand table part to around the arm hole on said operating table part; and said pad is connected to said fabric of said drape in such a manner that at least one-quarter inch of the outer edge of said pad is not fixedly attached to said fabric and can be bent up away from said fabric, making the clipping of clamps to said outer edge easier.

11. A surgical drape as in claim 9 wherein the width of said pad equals the distance between said two ends of said hinging connection.

12. A surgical drape as in claim 9 wherein said arm hole is located so that the length of the operating table part extends at least eighty inches on either side of said hole, enabling the drape to be used for surgery on either a left or right upper extremity.

* * * * *